United States Patent [19]

Thaw

[11] Patent Number: 4,740,707
[45] Date of Patent: Apr. 26, 1988

[54] PORTABLE TANNING UNIT

[76] Inventor: Allan Thaw, 152 Harbor La., Massapequa Park, N.Y. 11762

[21] Appl. No.: 923,649

[22] Filed: Oct. 27, 1986

[51] Int. Cl.⁴ .............................................. A61N 5/06
[52] U.S. Cl. .............................. 250/504 R; 250/494.1; 128/396
[58] Field of Search ........................ 250/504 R, 494.1; 128/396, 395; 362/450, 431

[56] References Cited

U.S. PATENT DOCUMENTS

| 1,660,794 | 2/1928 | Hudson. | |
|---|---|---|---|
| 3,646,349 | 2/1972 | Rietveld | 250/86 |
| 4,220,981 | 9/1980 | Koether | 362/431 |
| 4,335,724 | 6/1982 | Frei et al. | 128/395 |
| 4,624,259 | 11/1986 | Welt | 128/396 |
| 4,651,263 | 3/1987 | Hancock | 250/494.1 |

FOREIGN PATENT DOCUMENTS 2116685 9/1983 United Kingdom ............ 250/504 R

Primary Examiner—Craig E. Church
Assistant Examiner—Jack I. Berman
Attorney, Agent, or Firm—Spencer & Frank

[57] ABSTRACT

A tanning unit has a box-shaped base having top, bottom and lateral faces and a column assembly held by the base at one end and formed of a plurality of end-to-end arranged columns connected movably relative to one another. There is further provided a canopy which is secured to an opposite end of the column assembly and which is composed of a plurality of hingedly interconnected panels angularly adjustable relative to one another. Each panel supports an ultraviolet radiation source formed of a plurality of side-by-side arranged ultraviolet fluorescent tubes. The canopy has a closed position in which the panels are in a superposed relationship, with the light sources of adjoining superposed panels oriented face-to-face to one another. The tanning unit has a folded state in which the canopy is in its closed position and the columns are set in an angular position relative to one another such that the canopy is situated immediately adjacent the base in a face-to-face orientation therewith.

17 Claims, 3 Drawing Sheets

PORTABLE TANNING UNIT

BACKGROUND OF THE INVENTION

This invention relates to present-day ultraviolet tanning systems which, as a radiation source, include panels ("canopies") equipped with a great plurality—often several dozens—of side-by-side arranged ultraviolet fluorescent tubes which emit ultraviolet rays of relatively long wavelength, thus producing a "gentle"—and therefore relatively safe—ultraviolet radiation to effect gradual tanning.

Such systems have been recently widely used as permanent installations in health clubs, tanning clinics and similar organizations.

Tanning systems of the above-outlined type known heretofore have required relatively cumbersome, generally immovable equipment not adapted for use in the average home because of their significant spatial requirement, immobility and expense.

SUMMARY OF THE INVENTION

It is an object of the invention to provide a tanning unit, equipped with a conventional radiation source formed of a large number of parallel-arranged ultraviolet fluorescent tubes, which is of a collapsible (foldable) construction to present, in the collapsed state, a compact, self-protecting, easily portable unit and which, in the erected, operating state is, to a great extent, adaptable to emit rays in a direction and from a position which may be variable at will between wide limits.

This object and others to become apparent as the specification progresses, are accomplished by the invention, according to which, briefly stated, the tanning unit has a box-shaped base having top, bottom and lateral faces and a column assembly having a first end held by the base. The column assembly is formed of a plurality of end-to-end arranged columns connected movably relative to one another. There is further provided a canopy which is secured to an opposite, second end of the column assembly. The canopy is composed of a plurality of hingedly interconnected panels angularly adjustable relative to one another. Each panel supports an ultraviolet radiation source formed of a plurality of side-by-side arranged ultraviolet fluorescent tubes. The canopy has a closed position in which the panels are in a superposed relationship, with the light sources of adjoining superposed panels oriented face-to-face to one another. The tanning unit has a folded state in which the canopy is in its closed position and the columns are set in an angular position relative to one another such that the canopy is situated immediately adjacent the base in a face-to-face orientation therewith.

DESCRIPTION OF THE PREFERRED EMBODIMENTS

Figure 1:
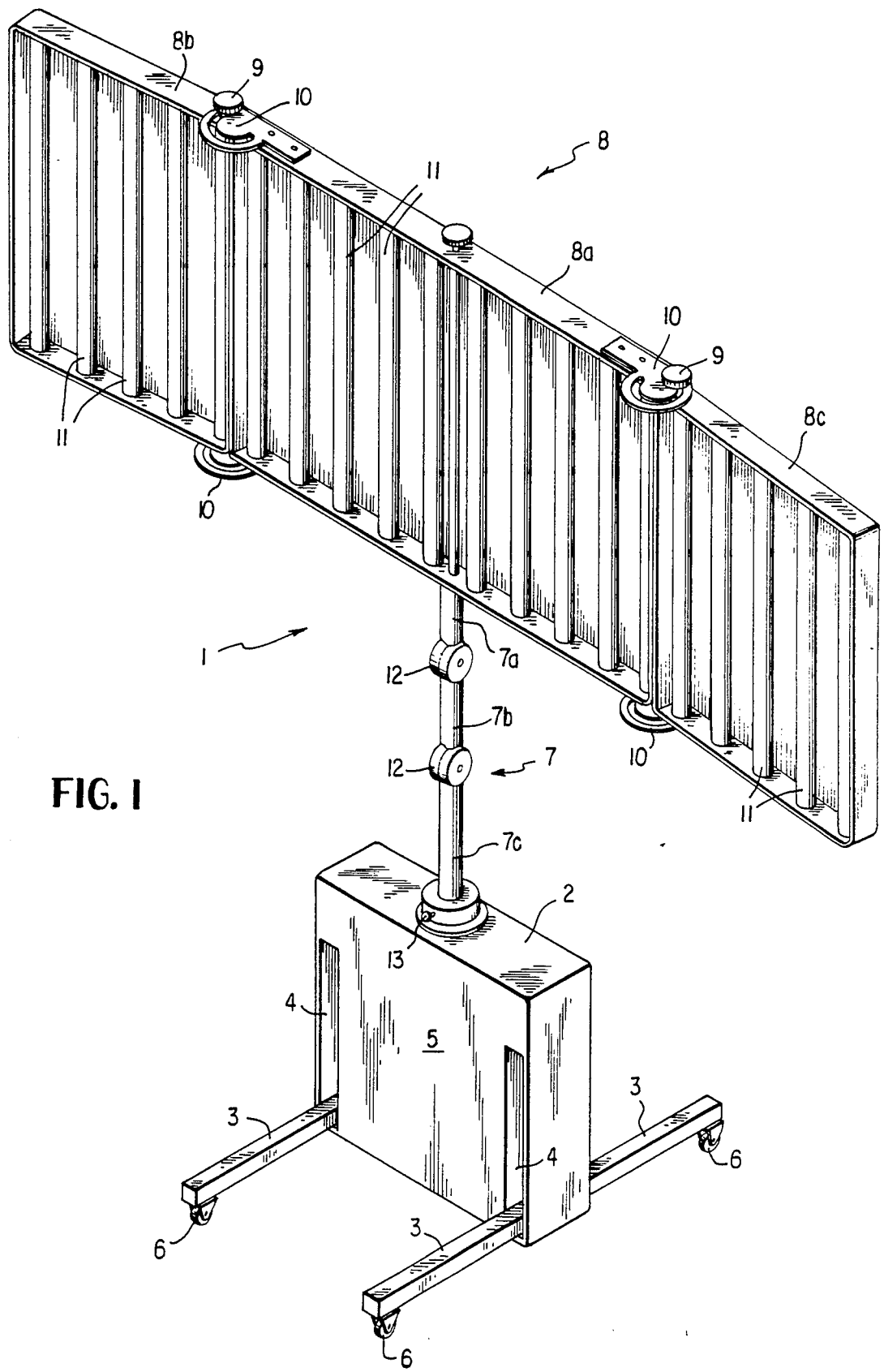
FIG. 1 is a perspective view of a preferred embodiment of the invention, shown in an operating position.

Turning to FIG. 1, there is illustrated a portable, collapsible tanning unit 1 in an erected, operating state.

The portable tanning unit 1 has a generally rectangular, flat, box-shaped base 2 which serves as a support and pedestal for the essential components of the unit 1. In order to increase the stability of the base 2, the latter is equipped with legs 3 which are, at one end, pivotally attached to a bottom part of the base 2 in a symmetrical distribution. The legs 3 may assume an extended, operative position as shown in FIG. 1, or a folded position in which they are received in wells 4 of the base 2 to be substantially flush with the respective opposite faces 5 thereof. The base 2 is stably supported on the ground by the extended legs 3 with the interposition of casters 6 (which may be of roller or sliding type) to provide for an easy displaceability of the unit when in the erected, operating state.

The base 2 supports, by virtue of a column assembly 7, a canopy 8 which is composed of a central canopy panel 8a secured to the column assembly 7 as well as flanking canopy panels 8b and 8c. The flanking canopy panels 8b and 8c are hinged along respective edges to opposite sides of the central canopy panel 8a and may be immobilized in a desired angular position with respect to the central canopy panel 8a by means of manually operable tightening knobs 9 threadedly received in a respective edge portion of the flanking canopy panels 8b and 8c and cooperating with rigid, arcuate, strip-like clamping plates 10. Each clamping plate 10 is affixed to the central canopy panel 8a and has an arcuate slot through which the shaft of the respective tightening knob 9 passes. Each canopy panel 8a, 8b and 8c supports a plurality of ultraviolet light sources, such as fluorescent tubes 11 in a parallel, side-by-side arrangement. Each flanking canopy panel 8b and 8c may be set at any position with respect to the central canopy panel 8a between and including a first limit position in which it is coplanar with the central canopy panel 8a and constitutes a continuation thereof and a second limit position in which it has been pivoted substantially 180° inwardly from the first limit position onto the frontal face of the central canopy panel 8a. As seen in FIG. 1, the canopy 8 has parallel pivotal axes about which the canopy panels can swing relative to one another and which are parallel to the width and perpendicular to the length of the canopy.

Figure 2:
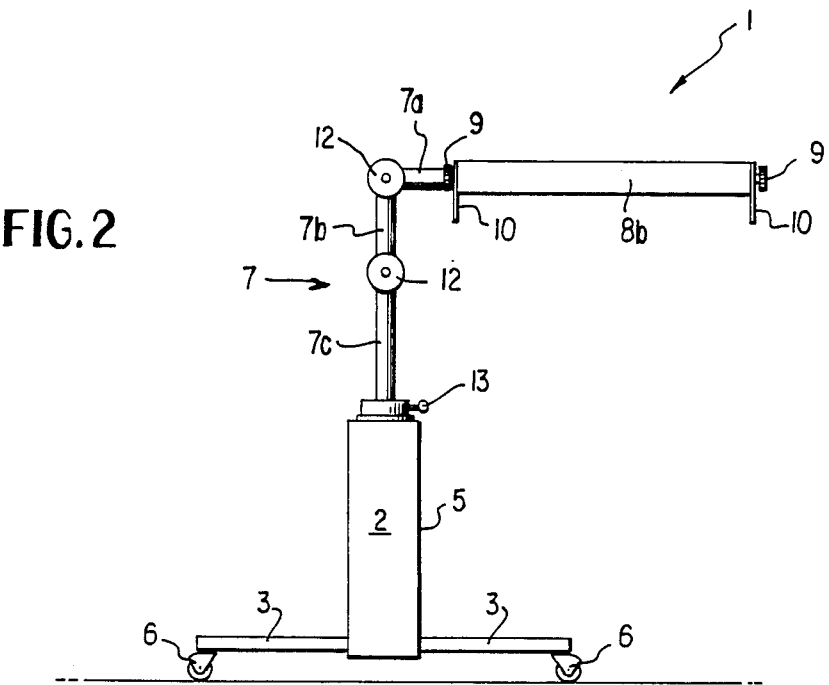
FIG. 2 is a side elevational view of the same embodiment, shown in an operating position different from that depicted in FIG. 1.

Also referring to FIG. 2, the column assembly 7 is formed of columns 7a, 7b and 7c articulated to one another end to end by pivot joints 12 which permit the three columns 7a, 7b and 7c to pivot in a common plane and to assume desired angular positions relative to one another. The columns 7a, 7b and 7c may be of circular or polygonal cross section. The pivot joints 12 are of the conventional type and may be of the universal joint type. They provide sufficient friction at the articulation thus ensuring that the angular position between the columns remains unchanged until altered on purpose. Such frictional force in each joint 12 may be provided by a releasable conventional tightening knob, ring or wing nut (not shown). The column 7a is secured to the central canopy panel 8a at the longitudinal middle thereof (the length of the panel being measured perpendicularly to the length dimension of the ultraviolet fluorescent tubes 11), while the column 7c is held at a center part of the top side of the base 2. The column 7c may telescope relative to the base 2 and may be immobilized in any desired longitudinal position by a conventional clamping device 13. Advantageously, the canopy 8 may turn about a longitudinal axis which coincides with the longitudinal axis of the column 7a and also, the column 7c may advantageously be turned about its own longitudinal axis. The sockets for supporting the ultraviolet fluorescent tubes 11 in the canopy panels as well as the electric cable connections are mounted in a conventional manner and are passed inside the column assembly 7 to the base 2 where the usual ballast transformers for the fluorescent tubes are disposed. On an outer face of the base 2 a timer, an energizing switch as well as an on-off indicator (none shown) may be mounted.

By virtue of the plurality of pivotal joints as well as possibilities for a turning motion about the longitudinal axis of components of the column assemby, the canopy 8 may be set to a great variety of positions relative to the base 2 to ensure a substantial versatility in positioning the light source to suit the user. Thus, in the position illustrated in FIG. 1, for example, the upper body parts and face of the user could be best exposed and, by virtue of the pivotal motion of the flanking canopy panels 8b and 8c an at least partial "wraparound" effect of the radiation source may be achieved. Further, in the adjusted position shown in FIG. 2—in which the canopy panels are brought into a coplanar arrangement in a horizontal plane—the unit is particularly suitable to irradiate the user in a lying position.

Figure 3:
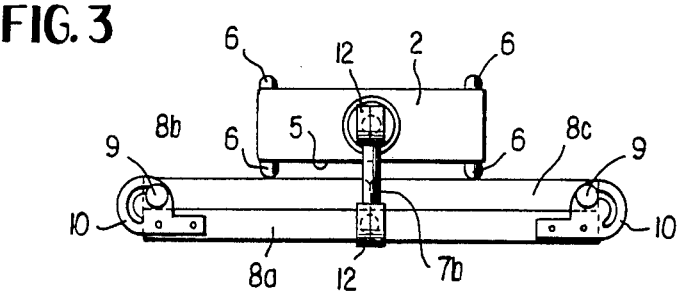
FIG. 3 is a top plan view of the preferred embodiment in a folded state.
Figure 4:
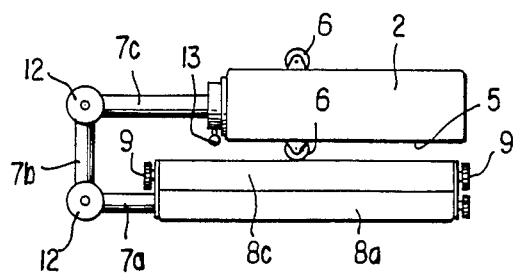
FIG. 4 is a side elevational view of the preferred embodiment in the folded state shown in FIG. 3.

Turning now to FIGS. 3 and 4, the portable tanning unit 1 is shown therein in a folded, collapsed state. As seen, the canopy 8 is closed which is achieved by pivoting inwardly the flanking canopy panels 8b and 8c onto the central canopy panel 8a. By designing the length—measured perpendicularly to the ultraviolet fluorescent tubes 11—of the flanking canopy panels such that the sum of their length equals the length of the central canopy panel 8a, the frontal face of the panels will be unexposed and thus all ultraviolet tubes protected in the closed position of the canopy 8. The legs 3 are pivoted to assume their position in the respective well 4, the telescoping column 7 is lowered into the base 2 to an appropriate height, and the column 7b is pivoted about 90° relative to the column 7c from a position shown in FIG. 2 so that the closed canopy 8 assumes a side-by-side, parallel position with a large face 5 of the base 2. In the folded position shown in FIGS. 3 and 4, the unit 1 is readily portable, for example, by grasping the same at the column 7b which, for this purpose, serves as a handle. For further protection in transport, the portable tanning unit 1 may be placed in an appropriate carrying case (not shown).

By way of example, the canopy 8, with the panels in a coplanar relationship, may measure 2 m×0.65 m, making the canopy adapted to receive ultraviolet fluorescent tubes of a length of 2 feet. Further, the base 2 may have a height of about 0.5 m, a width of 0.45 m and a depth of 0.15 m.

Figure 5:
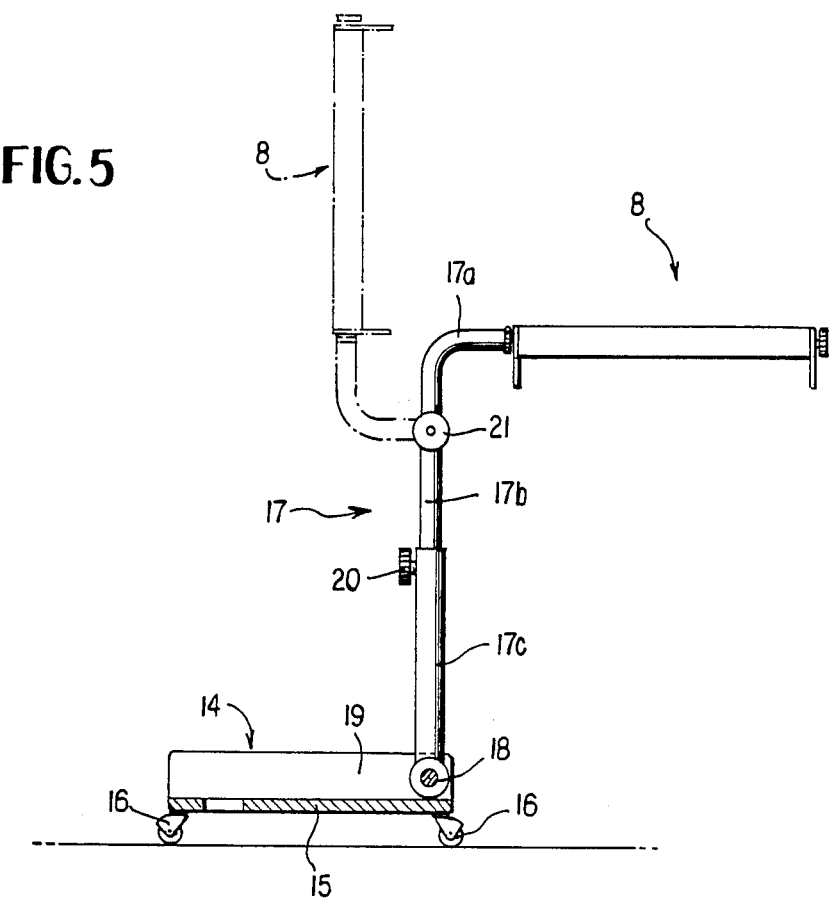
FIG. 5 is a side elevational view of a further preferred embodiment of the invention illustrated in an operating state.
Figure 6:
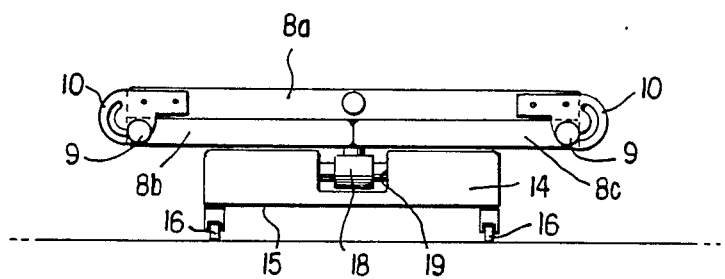
FIG. 6 is a front elevational view of the embodiment shown in FIG. 5, illustrated in a folded state.
Figure 7:
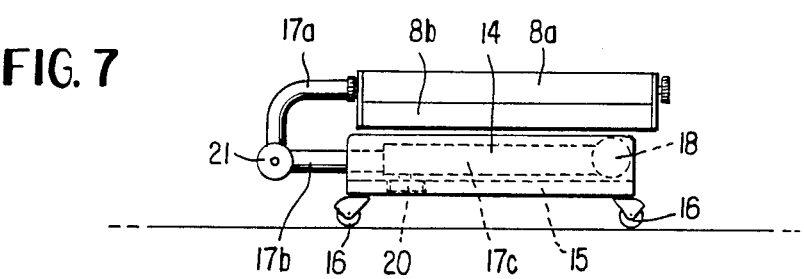
FIG. 7 is a side elevational view of the structure depicted in FIG. 6.

Turning now to FIGS. 5, 6 and 7, there is illustrated therein a further preferred embodiment of the invention, comprising a base 14 which has a flat, rectangular box-like structure, on one large surface 15 of which casters 16 are directly mounted. Thus, contrary to the arrangement according to the first-described embodiment, the base 14 is arranged with its large dimension parallel to the supporting surface (ground). A column assembly 17 formed of consecutive columns 17a, 17b and 17c is held on the base 14. For this purpose, one end of the column 17c is attached, by a pivotal joint 18, to one end of the base 14, at the middle of the side thereof. The column 17c may be pivoted in a vertical plane between a horizontal and vertical position. In the horizontal position, that is, when the column 17c extends parallel to the base 14, it is received in a central well 19 thereof as shown in FIGS. 6 and 7. The column 17b is telescopically received in the column 17c and may be immobilized with respect thereto in a desired position by means of a tightening knob 20. The column 17a is elbow-shaped; at one end it is pivotally attached to an end of the column 17b by means of a pivotal joint 21 while its other end is secured to the canopy 8 in a manner similar to the arrangement described in the previous embodiment illustrated in FIGS. 1–4.

In the erected, operating position illustrated in FIG. 5, the canopy 8 is set to a generally horizontal orientation adapted to irradiate a person lying underneath. By pivoting the elbow column 17a counterclockwise by 90° from the position shown in FIG. 5, the canopy will be set upright in the phantom-line position, adapted to irradiate a person's upper body and face, particularly when seated. By providing that the column is rotatable about its longitudinal axis (in the loosened position of the knob 20), the canopy 8 may be swung into a desired position in a plane perpendicular to the plane of FIG. 5.

FIGS. 6 and 7 show two sides of the portable tanning unit of the second preferred embodiment in a collapsed, folded state in which, similarly to FIGS. 3 and 4 of the first embodiment, the closed canopy extends adjacent and parallel to the base 14.

It will be understood that the above description of the present invention is susceptible to various modifications, changes and adaptations, and the same are intended to be comprehended within the meaning and range of equivalents of the appended claims.

What is claimed is:

1. A tanning unit emitting ultraviolet radiation comprising, in combination,
a box-shaped base having top, bottom and lateral faces; a column assembly formed of a plurality of end-to-end arranged columns connected angularly movable relative to one another; said column assembly having a first end supported by said base and an opposite, second end; a canopy secured to said second end of said column assembly; said canopy being composed of a plurality of hingedly interconnected panels angularly adjustable relative to one another; each panel supporting an ultraviolet radiation source formed of a plurality of side-by-side arranged ultraviolet light sources; said canopy having a closed position in which said panels are in a superposed relationship, with the light sources of adjoining superposed panels oriented face-to-face to one another; said tanning unit having a folded state in which said canopy is in its said closed position and said columns are set in an angular position relative to one another such that said canopy is situated immediately adjacent said base in a face-to-face orientation therewith.

2. A tanning unit as defined in claim 1, further comprising manually tightenable and releasable clamping means for immobilizing said panels in a desired angular position relative to one another.

3. A tanning unit as defined in claim 1, wherein one of said panels is a central panel attached to one column of said column assembly and two of said panels are flanking panels hingedly attached to opposite sides of said central panel; said flanking panels being pivotal relative to said central panel about respective axes extending parallel to one another along said opposite sides of said central panel.

4. A tanning unit as defined in claim 1, wherein said base has opposite large faces and interposed small faces; said panels having a substantially flat configuration; in said folded state said canopy being situated face-to-face with one of said large faces of said base.

5. A tanning unit as defined in claim 4, wherein said large faces are two of said lateral faces; said columns are three in number; one column being a central column and two columns being flanking columns; in said folded state of said tanning unit said central column extending perpendicularly to said large faces and said flanking columns extending parallel to said large faces.

6. A tanning unit as defined in claim 4, wherein said column assembly is arranged for partially telescoping into and out of said base.

7. A tanning unit as defined in claim 4, wherein said large faces constitute two of said lateral faces; further comprising a plurality of elongated legs each having one end pivotally secured to said base at the bottom face thereof; each said leg having a first pivotal position and a second pivotal position; in said first pivotal position each leg extending generally perpendicularly to and away from said large faces and in said second pivotal position each leg extending parallel and face-to-face to respective said large faces; in said folded state of said tanning unit said legs being in said second pivotal position.

8. A tanning unit as defined in claim 7, further comprising elongated wells formed in said large faces; a separate said well being associated with each said leg for receiving an associated said leg in the second pivoted position thereof to assume a flush relationship with respective said large faces.

9. A tanning unit as defined in claim 7, further comprising caster wheels mounted on said legs.

10. A tanning unit as defined in claim 4, wherein said large faces are said top and bottom faces; further comprising pivot means for attaching said one end of said column assembly to said base, adjacent a bounding edge thereof, for a pivotal motion in a plane perpendicular to said top face.

11. A tanning unit as defined in claim 10, further comprising caster wheels mounted on said bottom face.

12. A tanning unit as defined in claim 10, further comprising an elongated, upwardly open, channel-like well extending in said base and arranged for receiving a length portion of said column assembly in the folded state of said unit.

13. A tanning unit as defined in claim 12, wherein a first one of said columns includes said end connected to said pivot means; a second one of said columns being telescopically connected to the first column; and a third one of said columns being of elbow shape and having one end pivotally connected to said second column and another end carrying said canopy; said third column being pivotal in said plane relative to said second column.

14. A tanning unit as defined in claim 4, wherein said large faces constitute two of said lateral faces; further comprising a plurality of elongated legs each having one end secured to said base at the bottom face therof; each leg extending generally perpendicularly to and away from said large faces.

15. A tanning unit as defined in claim 7, further comprising caster means mounted on said legs for facilitating displacement of the tanning unit on a floor.

16. A tanning unit as defined in claim 10, further comprising caster means mounted on said bottom face for facilitating displacement of the tanning unit on a floor.

17. A tanning unit as defined in claim 1, wherein said canopy has parallel pivotal axes about which said panels of the canopy are swingable; further wherein said canopy has a length dimension perpendicular to said pivotal axes and a width dimension parallel to said pivotal axes; said ultraviolet light sources are elongated, tubular, linear light bulbs having a length dimension oriented perpendicularly to the length dimension of said canopy.

* * * * *